United States Patent [19]

Nagai et al.

[11] Patent Number: 5,194,372
[45] Date of Patent: Mar. 16, 1993

[54] METHOD AND APPARATUS FOR DETECTING DISORDERS IN GENOMIC SUBSTANCES

[75] Inventors: Keiichi Nagai, Higashiyamato; Jiro Tokita, Fuchu, both of Japan

[73] Assignee: Hitachi, Ltd., Tokyo, Japan

[21] Appl. No.: 548,798

[22] Filed: Jul. 6, 1990

[30] Foreign Application Priority Data

Jul. 10, 1989 [JP] Japan .................................. 1-175465
Sep. 1, 1989 [JP] Japan .................................. 1-224419

[51] Int. Cl.$^5$ .......................... C12Q 1/68; C12Q 1/34; G01N 25/18; C07H 15/12
[52] U.S. Cl. ........................................... 435/6; 435/18; 436/800; 436/151; 536/24.31; 935/78; 935/76
[58] Field of Search ...................... 435/6, 18; 436/800, 436/151; 935/78, 76; 536/27

[56] References Cited

U.S. PATENT DOCUMENTS 4,711,955 12/1987 Word et al. ............................ 435/6

OTHER PUBLICATIONS

Brumbaugh et al., DBA Accession No.: 87–12683, Abstr. Pap. Am. Chem. Soc. (193 Meet., ENVR15) 1987.
Lopez–Galindez et al., Proc. Natl. Acad. Sci. USA 85(10), 1988 pp. 3522–3526.
Brumbaugh et al.: Proc. Natl. Acad. Sci., USA 85, 5610–5614, Aug., 1988.

*Primary Examiner*—Margaret Moskowitz
*Assistant Examiner*—Scott A. Chambers
*Attorney, Agent, or Firm*—Pennie & Edmonds

[57] ABSTRACT

Disorders of the base sequences in genomic substances such as DNA and RNA are detected by changing the state of aggregation of fine particles by cleavaging using a nuclease. A single-stranded denatured product of the objective genomic substance is added to first and second fine particles each attached to plural pieces of first and second single-stranded nucleic acid probes, respectively. The first and second single-stranded nucleic acid probes are complementary to a first region and a second region, respectively, on the objective genomic substance, which are exclusive of each other and contiguous from each other. Aggregations of the first and second fine particles are formed by double or multiple hybridization reaction of the denatured objective genomic substance added with the first and second single-stranded nucleic acid probes. The aggregations are then digested with a nuclease which cleaves the non-complementary-mismatch-containing portion of the double strand of each hybrid permitting the formation of the aggregations, in the vicinity of a mismatch-localized region, but substantially not the completely complementary portion of the double strand of the hybrid. The size of the aggregations in the digested solution is first measured and then the degree of mismatch between the complementary base sequences of the objective genomic substance and the first or second single-stranded nucleic acid probe is measured using the size of the aggregations.

4 Claims, 5 Drawing Sheets

METHOD AND APPARATUS FOR DETECTING DISORDERS IN GENOMIC SUBSTANCES

BACKGROUND OF THE INVENTION

1. FIELD OF THE INVENTION

The present invention relates to method and apparatus for diagnoses by detection of disorders in genomic substances of organisms, which use a molecular biological technique.

2. RELATED ART STATEMENT

A method for detecting disorders in genomic substances by the use of a nuclease is discussed in Nature 313 (1985) pp 495–498. In this method, whether a hybrid between a target DNA fragment and a DNA probe is complete or incomplete is investigated. This method is characterized in that S1 nuclease is used for detecting an incomplete portion. S1 nuclease digests only single-stranded DNA but not double-stranded DNA. Therefore, when hybridization between a target genomic substance fragment and a DNA probe is complete and they form a double strand, the resulting hybrid is not digested. On the other hand, when the hybridization is not complete and a single-stranded portion exists, the resulting hybrid is digested and shortened. Accordingly, disorders in a target DNA fragment can be detected by forming a hybrid between the target DNA fragment and a DNA probe labeled with a radioisotope or the like, treating the hybrid with S1 nuclease, measuring the molecular weight of the hybrid by electrophoresis, and judging whether the hybrid is complete or incomplete.

In addition, this method is applied to hybrids formed between target DNA or RNA fragments and RNA probes, by the use of a nuclease RNase A, as discussed in Science 230 (1985) pp 1242–1246 and Proc. Natl. Acad Sci. U.S.A. 82 (1985) pp 7575–7579.

OBJECT AND SUMMARY OF THE INVENTION

In the above related arts, automation and apparatus development are not taken into consideration and radioisotopes are used for labeling. Moreover, products of digestion with nuclease are electrophoresed and then measured by autoradiography which is a method requiring much labor and time.

It is an object of the present invention to provide method and apparatus which permit comprehensive and highly reliable diagnosis of disorders such as single base substitution, insertion and deletion in genomic substances, by providing a measuring means suitable for automation of apparatus and realizing a detecting means using a non-radioactive label.

The present invention is as follows. A nucleic acid probe is previously labeled with a fluorophore or an enzyme capable of making its substrate into a fluorophore. A hybrid between the nucleic acid probe and a target genomic substance is formed and then treated with a nuclease capable of decomposing and digesting the mismatch portion of the hybrid. Consequently, the nucleic acid probe forming the hybrid with the target genomic substance including disorders is cleaved. In the present invention, as a first method, in analyzing the change of the molecular weight caused by the cleavage, of the nucleic acid probe or the hybrid between the nucleic acid probe and the target genomic substance by electrophoresis, the label fluorophore during electrophoresis is detected by the laser induced fluorescence method, whereby the molecular weight analysis of the nucleic acid probe or the hybrid between the nucleic acid probe and the target genomic substance is carried out in a short time. Accordingly, autoradiography becomes unnecessary and it becomes possible to obtain an analysis result only by loading a sample on an electrophoretic plate. Therefore, labor and time can be greatly saved. As a second method, by the labeling of the nucleic acid probe with the fluorophore or the enzyme capable of making its substrate into a fluorophore, the label fluorophore or the fluorophore converted from the enzyme is detected by the laser induced fluorescence method after completion of the electrophoresis, whereby there is carried out the molecular weight analysis of the nucleic acid probe or the hybrid between the nucleic acid probe and the target genomic substance. Accordingly, autoradiography becomes unnecessary, so that time and labor can be saved. Although this method is less effective in reducing labor and time than the first method, it can realize measurement for a small amount of sample or improvement of the reliability of measurement because measurement is carried out after completion of the electrophoresis and hence much measurement time can be spent.

One aspect of the present invention comprises labeling a single-stranded nucleic acid probe complementary to the normal base sequence of an objective genomic substance fragment, with a fluorophore or an enzyme capable of making its substrate into a fluorophore, forming a hybrid between a single-stranded sample prepared by denaturing the genomic substance fragment and the labeled nucleic acid probe, subjecting the hybrid to enzymatic treatment with a nuclease which cleaves the non-complementary-mismatch-containing portion of the double strand of the hybrid, and substantially not the completely complementary portion of the double strand of the hybrid, allowing the enzyme-treated hybrid or single-stranded denatured products thereof to migrate in an electrophoretic lane, irradiating the electrophoretic lane with laser beams to excite the fluorophore labeling the single-stranded nucleic acid probe, detecting the fluorescence thus emitted to obtain information on the change of molecular weight of the hybrid caused by the enzymatic treatment, and thereby detecting disorders of the base sequence of the genomic substance fragment.

Preferably, the irradiation with laser beams is conducted in the direction of a predetermined position in the middle of the electrophoretic lane, and fluorescent is detected in the irradiation position during the migration.

In addition, the irradiation with laser beams is conducted on the electrophoretic lane after completion of the migration for a predetermined time, with scanning in a predetermined range of the electrophoretic lane.

As an electrophoretic carrier for the electrophoretic lane, a polyacrylamide gel is preferably used.

As the electrophoretic carrier for the electrophoretic lane, agarose gel may also be used.

As the electrophoretic lane, a capillary having a diameter of 1 mm or less is preferably used.

The nuclease is preferably S1 nuclease, more preferably RNase A.

The present invention includes the case where the labeling of the single-stranded nucleic acid probe is labeling of both ends of the probe.

The present invention includes a method in which the both ends of the single-stranded nucleic acid probe are preferably labeled with different fluorophores, respectively.

In addition, the present invention provides an apparatus for detecting disorders in genomic substances which comprises a means for electrophoresing a sample prepared by labeling a single-stranded nucleic acid probe complementary to the normal base sequence of an objective genomic substance fragment with a fluorophore or an enzyme capable of making its substrate into a fluorophore, forming a hybrid between the labeled single-stranded probe and the genomic substance fragment, and subjecting the hybrid to enzymatic treatment with a nuclease capable of cleaving the non-complementary mismatch portion of the double strand of the hybrid, a means for irradiating a predetermined position in the middle of the electrophoretic lane of the electrophoretic means with laser beams, a means for detecting fluorescence emitted at the time when the sample reaches the position of irradiation with laser beams, and a means for recording the time-course of detection output of the detecting means.

The present invention provides another method for detecting disorders in genomic substance which comprises preparing a solution containing at least a large number of first fine particles each having plural pieces of a first single-stranded nucleic acid probe attached thereto and a large number of second fine particles each having plural pieces of a second single-stranded nucleic acid probe attached thereto, the first and second single-stranded nucleic acid probes being complementary to a first region and second region, respectively, on an objective genomic substance which are exclusive of each other and contiguous to each other, adding a single-stranded denatured product of the objective genomic substance, forming aggregations of the first and second fine particles in the solution by double or multiple hybridization reaction of the denatured objective genomic substance added with the first and second single-stranded nucleic acid probes, digesting the solution containing the aggregations with a nuclease which cleaves the non-complementary-mismatch-containing portion of the double strand of each hybrid permitting the formation of the aggregations, in the vicinity of a mismatch-localized region, but substantially not the completely complementary portion of the double strand of the hybrid, measuring the size of aggregations in the digested solution, and thereby measuring the degree of mismatching between the complementary base sequences of the objective genomic substance and the first or second single-stranded nucleic acid probe.

Preferably, there is measured the difference of the sizes of the aggregations in the solution before and after the digestion.

The measurement of size of the aggregations in the solution is conducted preferably by measuring the intensity of scattered light generated by irradiation of the solution with laser beams.

The present invention include a method in which the measurement of size of the aggregations in the solution is conducted more preferably by measuring a photoacoustic signal given by irradiation of the solution with modulated laser beams.

In addition, the above-mentioned first and second nucleic acid probes may be complementary to a first region and a second region, respectively, on an objective genomic substance which are exclusive of each other and apart from each other. In this case, it is necessary to add unit nucleotide triphosphates which constitute the aforesaid objective genomic substance to a solution containing aggregations formed, before digestion to subject the same to complementary chain elongation reaction with a single-stranded portion permitting formation of the aggregations, and thereby make the single-stranded portion into a double-stranded hybrid.

Accordingly, the present invention provides a still other method for detecting disorders in genomic substances which comprises preparing a solution containing at least a large number of first fine particles each having plural pieces of a first single-stranded nucleic acid probe attached thereto and a large number of second fine particles each having plural pieces of a second single-stranded nucleic acid probe attached thereto, the first and second single-stranded nucleic acid probes being complementary to a first region and a second region, respectively, on an objective genomic substance which are exclusive of each other and contiguous to each other, adding a single-stranded denatured product of the objective genomic substance, forming aggregations of the first and second fine particles in the solution by double or multiple hybridization reaction of the denatured objective genomic substance added with the first and second single-stranded nucleic acid probes, adding unit substances which constitute the objective genomic substance to the solution containing the formed aggregations to make the strands permitting the formation of the aggregations, into double-stranded hybrid, digesting the solution containing the aggregations with nuclease which cleaves the non-complementary-mismatch-containing portion of the double strand of the hybrid, in the vicinity of a mismatch-localized region, but substantially not the completely complementary portion of the double strand of the hybrid, measuring the size of aggregations in the digested solution, and thereby measuring the degree of mismatching between the complementary base sequences of the objective genomic substance and the first or second single-stranded nucleic acid probe.

The present invention includes a method in which the difference of the sizes of the aggregations in the solution before and after the digestion is preferably measured.

In addition, the measurement of size of the aggregations in the solution is conducted by measuring the intensity of scattered light generated by irradiation of the solution with laser beams.

Further, the measurement of size of the aggregations in the solution is conducted by measuring a photoacoustic signal given by irradiation of the solution with modulated laser beams.

Still further, the unit substances are preferably nucleotide triphosphates.

In addition, the present invention includes a method in which the single-stranded portion is preferably made into a double-stranded hybrid by complementary chain elongation reaction.

Other characteristics of the present invention will become apparent from the description of Example.

EXAMPLE

One example of the present invention is explained below with reference to FIGS. 1A and 1B, FIG. 2 and FIGS. 3A to 3D.

Figure 1A:
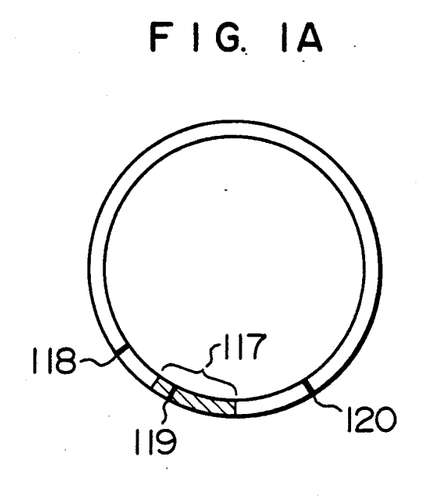
FIGS. 1A and 1B are schematic illustrations of DNA samples used for confirming the present invention.
Figure 1B:
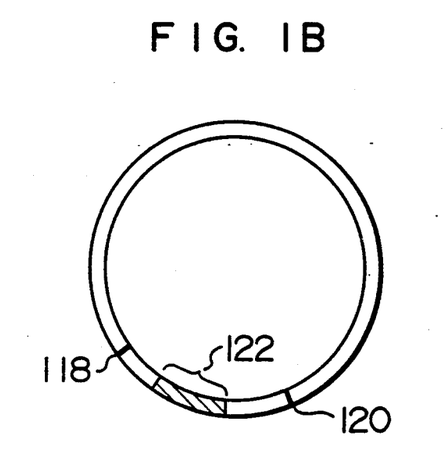

In this example, a plasmid M13 RF was used as a DNA sample. FIG. 1A shows normal M13 RF. M13 plasmid contains a part of β-galactosidase gene and 9 other genes. In this example, the β-galactosidase gene shown by the signal 117 in FIG. 1A was used as target gene. On the other hand, for confirming the effect of the invention, artificially prepared M13 RF not having 6 bases of the β-galactosidase gene was used as a DNA sample containing a modified gene. It was prepared by cleaving the above-mentioned normal DNA sample with a restriction enzyme Mst II at the site shown by the signal 119 in FIG. 1A of β-galactosidase gene, and then digesting the resulting cohesive ends with S1 nuclease to blunt the same, followed by recombination by the use of T4 DNA ligase. The thus obtained M13 containing a modified gene 122 is shown in FIG. 1B. It is also possible to cleave the normal DNA sample at the sites 118 and 120 shown in FIG. 1A and FIG. 1B with restriction enzymes, for example, Bgl II and Nar 1, respectively, to obtain DNA samples which are individually not in the form of a ring.

A DNA probe was synthesized by the phosphoamidide method. The probe was a DNA fragment having a length of 40 bases and containing a base sequence complementary to the above-mentioned deleted 6-base region, at the positions 16 to 26 from the 5'-end, and its base sequence was completely complementary to normal M13. A fluorochrome was introduced into the 5'-end of this synthetic DNA by introduction of an amino group by the method of L. M. Smith et al. On the other hand, a fluorochrome was introduced into the 3'-end by forming a phosphoric ester linkage. Three DNA probes with different labels were synthesized. The first probe was a probe having fluorescein isothiocyanate (FITC) attached to the 5'-end. The second probe was a probe having FITC attached to each of the 5'-end and the 3'-end. The third probe is a probe having FITC attached to the 5'-end and Texas Red attached to the 3'-end.

Each of the above target DNA samples was denatured into single-stranded DNA by heating, after which each of the above DNA probes was added and the reaction was carried out under hybridization conditions to from a hybrid. S1 nuclease was added to the reaction solution to carry out cleavage reaction of the mismatch portion of the hybrid.

After completion of the cleavage reaction, the reaction product was denatured by heating to bring the DNA sample into single-stranded state. The sample thus obtained was electrophoresed by means of the apparatus shown in FIG. 2, and the fluorescent labeling substance was detected by the laser induced fluorescence method.

Figure 2:
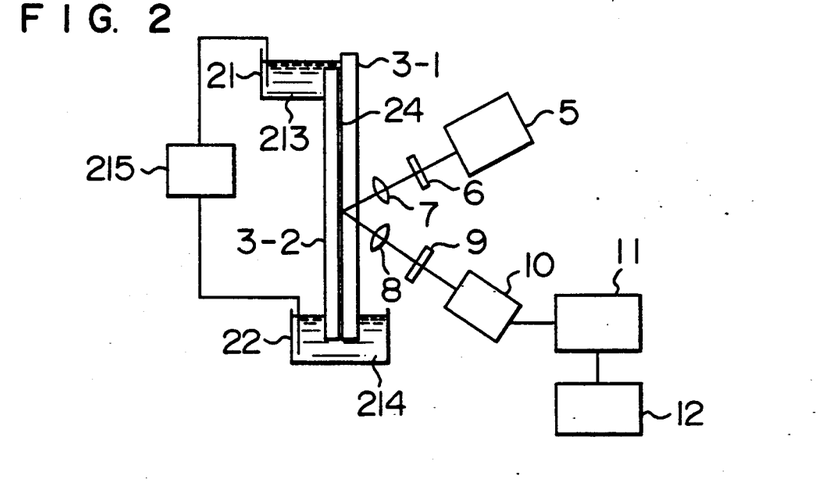
FIG. 2 is a block diagram showing an apparatus of one example of the present invention.

In detail, an upper electrolite 213 into which the sample has been poured is placed in an upper buffer tank 21. A potential difference is applied between the upper electrolyte and a lower electrolyte 214 placed in a lower buffer tank 22, by means of an electric source 215, whereby an electric field is applied to a gel 24 spread over both electrolytes, and the sample migrates in the gel. The gel 24 used is a 12% polyacrylamide gel which is held between supporting plates 3-1 and 3-2 made of quartz plate.

The apparatus shown in FIG. 2 is designed to excite the fluorophore label of a sample (each DNA probe, in this case) migrating down, at a distance of migration of 20 cm, namely, at 20 cm distance from the top of the gel 24, detect the fluorescence thus emitted, and record its change with the lapse of time. In detail, laser beams from an argon ion laser 5 are casted on the position described above of the gel 24 through a filter 6 and a lens 7. Fluorescence from said position is passed through a lens 8 and a filter 9 and detected by a photodetector 10. As the photodetector 10, a photomultiplier is preferable. FITC is detected preferably by the use of light of 488 nm, and Texas red preferably by the use of light of 515 nm. The third DNA probe labeled with the above two fluorophores is detected by alternating the filter 6 and the filter 9 mechanically. The detection output from the photodetector 10 is introduced into a data processor 11, and its change with the lapse of time is recorded by a recorder 12.

Figure 3A:
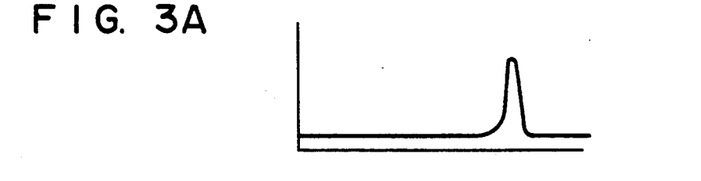
FIGS. 3A to 3D are time charts showing the results of electrophoresis according to the above example.
Figure 3B:
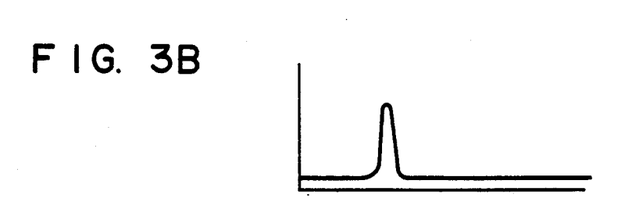
Figure 3C:
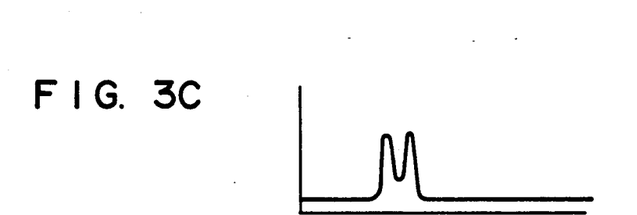
Figure 3D:
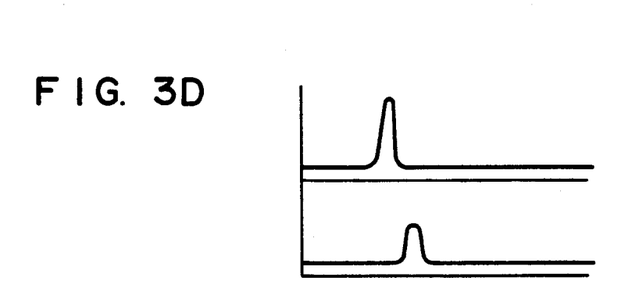

FIGS. 3A to 3D show the results of analyzing various samples for electrophoresis subjected to cleavage reaction by nuclease and then denaturation by heating, by electrophoresis by means of the apparatus shown in FIG. 2. In each figure, the axis or ordinate refers to fluorescence intensity and the axis of abscissa to time. FIG. 3A shows a result for a sample for electrophoresis obtained by reacting the normal DNA with the first DNA probe. FIG. 3B shows a result for a sample for electrophoresis obtained by reacting the abnormal DNA lacking 6 bases with the first DNA probe. In FIG. 3B, the migration time is shorter than in FIG. 3A, namely, the length of the DNA probe in terms of the number of bases is reduced by the cleavage reaction. From this fact, it can be seen that disorders of the base sequence of DNA sample can be detected by the process described above and analysis of migration time. On the other hand, FIG. 3C shows a result for a sample for electrophoresis obtained by reacting the abnormal DNA with the second DNA probe. Since both ends of the second DNA probe have been labeled, there are detected two peaks indicating the migration times of two DNA probe fragments separated by cleavage, respectively. FIG. 3D shows results for a sample for electrophoresis obtained by reacting the abnormal DNA with the third DNA probe: the upper part shows a result obtained by the use of a filter for light of 488 nm, and the lower part shows a result obtained by the use of a filter for light of 515 nm. Since the ends of the third DNA probe have been labeled with different fluorophores, respectively, the migration times of two DNA probe fragments separated by cleavage can be individually measured. From this fact, it can be seen that employment of the second or third DNA probe is sufficient for knowing the position or degree of disorder in DNA sample, and that in particular, employment of the third DNA probe makes it possible to know them more accurately.

The present example is effective in that disorders in a target genomic substance can be rapidly and easily detected without using a radioisotope and without requiring a procedure such as autoradiography.

When a DNA probe having a length of hundreds of bases or more is used, it is preferable in some cases to use agarose gel.

Figure 4:
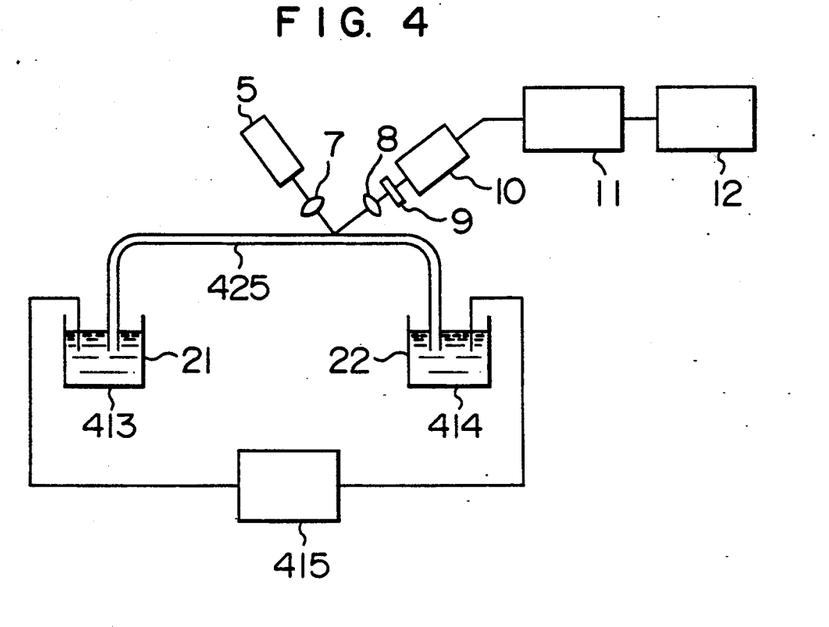
FIG. 4 and FIGS. 5A and 5B are a block diagram showing another example and time charts showing the results of electrophoresis according the another example, respectively.

Another example of the present invention is explained below with reference to FIG. 4. In this example, as an electrophoretic medium, there was used an electrolyte in a capillary 425 made of molten quartz, but not a gel. In detail, an electrolyte 413 on the positive electrode side and an electrode 414 on the negative electrode side were connected to each other by a capillary 425. The capillary used had an inside diameter of 100 μm and a length of 80 cm. Detection was conducted at a distance of migration of 60 cm.

In this example, there were used the same target nucleic acids as in the example described above and the first probe described therein. In addition, there were used the same laser beam source and detecting optical system as in the example described above. Each sample was electrically injected in the electrolyte on the negative electrode side.

Figure 5A:
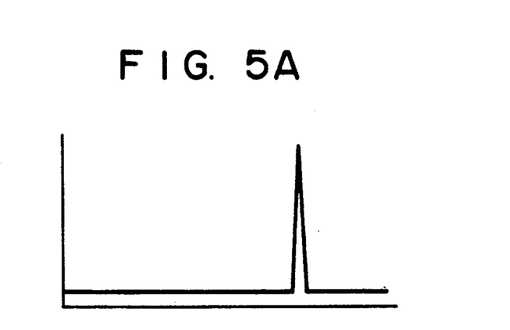
Figure 5B:
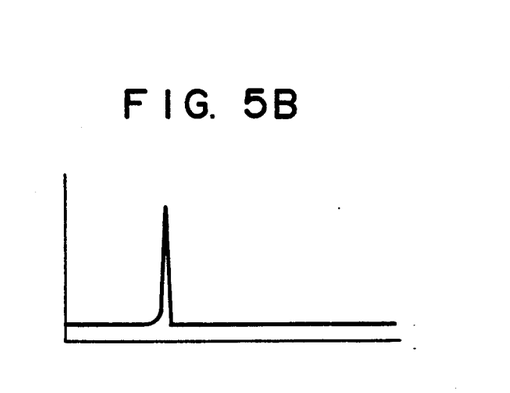

The detection signals obtained were as shown in FIGS. 5A and 5B. In the case of the normal target DNA, the signal shown in FIG. 5A was obtained. In the case of the abnormal target DNA, the signal shown in FIG. 5B was obtained. In the latter case, it can be seen that a hybrid between the target DNA and the DNA probe had been cleaved by S1 nuclease.

The present example is effective in that the measurement time is shorter than in the first example. The diameter of the capillary for electrophoresis should be 1 mm or less.

Figure 6:
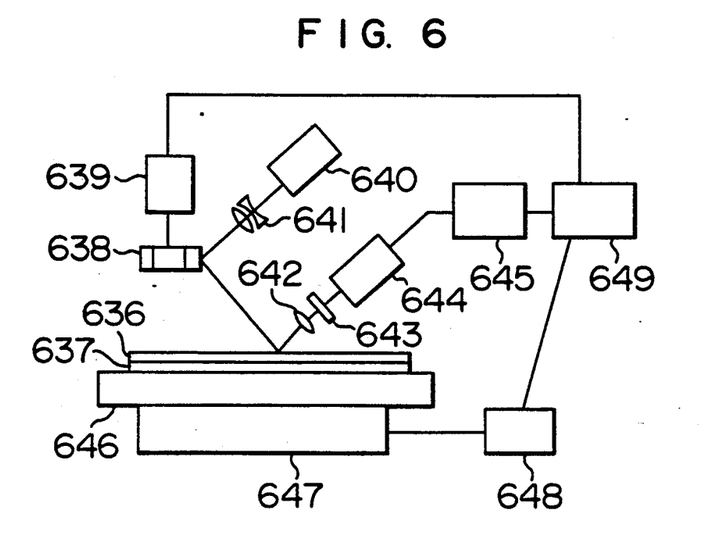
FIG. 6 is a block diagram showing yet another example.

Further another example of the present invention is explained below with reference to FIG. 6. This example is different from the two examples described above in that in this example, a fluorophore labeling a DNA probe was detected after completion of electrophoresis.

In this example, a polyacrylamide gel 637 was used as an electrophoretic medium. There were used the same target DNA's and DNA probes as in the example described above. After completion of electrophoresis, supporting plates 636 made of quartz are placed on a stage 646. Light from an argon ion laser 640 is scanned on the gel in a direction perpendicular to electrophoretic migration through a lens system 641 and a polyhedral mirror 638 driven by a means for driving the mirror 639. Fluorescence emitted by the gel in this case is passed through a lens system 642 and a filter 643 and detected by an one-dimentional photodetector 644. Scanning in the direction of electrophoretic migration is conducted by moving the stage 646 with high precision by means of a stage scanner 647 which movement is controlled by a means for controlling movement 648 and by a system controller 649. Using such an apparatus, the electrophoretic pattern of each DNA sample subjected to two-dimentional development in the electrophoretic gel was visualized, whereby the molecular weight of each DNA probe could be analyzed. The present example is effective in that highly sensitive measurement is possible because a longer measurement time than that in the preceding examples can be employed.

Next, there are described below several examples in which the state of aggregations of fine particles in a solution is changed by cleavage using a nuclease, whereby disorders in genomic substances are detected. These examples require two nucleic acid probes which are complementary to two mutually exclusive regions, respectively, of a target genomic substance. As samples in which disorders are to be detected, DNA samples are used as in the examples explained with reference to FIGS. 1 to 6.

First, two DNA probes are synthesized by the phosphoamidide method. The first DNA probe is a DNA fragment having a length of, for example, 40 bases which is completely complementary to a first region of a normal DNA sample. The second DNA probe is a DNA fragment having a length of 40 bases which is completely complementary to a second region contiguous to the first region of the DNA sample. The first and second DNA probes are preferably exclusive of each other. That is, the first DNA probe is preferably not complementary to the second region of the DNA sample, and the second DNA probe is preferably not complementary to the first region. The sum of the first and second regions (total length: 80 bases) is a gene range in which disorders are to be detected.

Figure 7A:
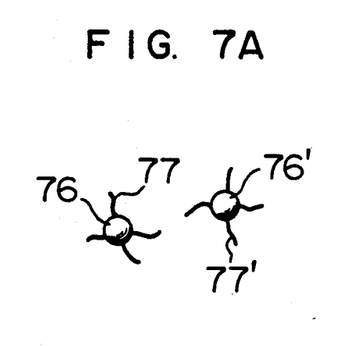
FIGS. 7A and 7B are schematic illustrations of formation of aggregations by fine particles.

The DNA probes are individually purified by a high-performance liquid chromatography (HPLC). On the other hand, for example, polystyrene fine particles having a diameter of 300 nm are divided into two groups, and plural pieces of the first DNA probe are fixed on each fine particle in one group through a linker made of poly A having a length of 20 bases. Plural pieces of the second DNA probe are fixed on each fine particle in the other group through the same linker as described above. The thus treated fine particles in the two groups are mixed with a solution to prepare a reaction mixture for examination in which there are suspended the fine particles 76 having the first DNA probe 77 fixed thereon as shown in FIG. 7A and the fine particles 76' having the second DNA probe 77' fixed thereon as shown in FIG. 7A. The aforesaid fine particles may be made of any of materials other than polystyrene, such as glass, nylon, rubber, other chemical substances, or substances in living body, e.g. erythrocyte. Various techniques can be employed for fixing the DNA probes.

Figure 7B:
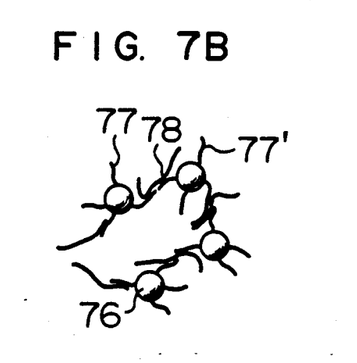
Figure 8A:
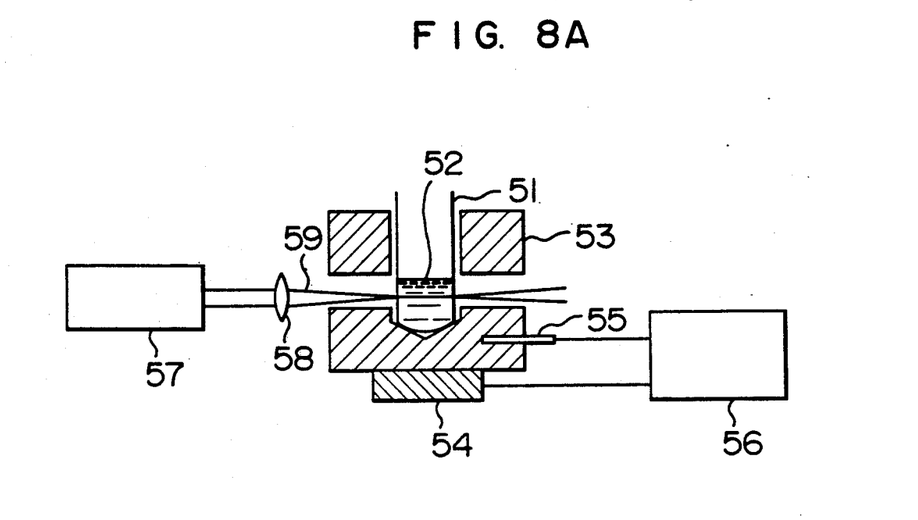
FIGS. 8A and 8B are a longitudinal sectional view and a tranverse sectional view, respectively, of an apparatus used in still another example of the present invention.

The aforesaid reaction mixture 52 and a single-stranded DNA obtained by denaturing the DNA sample are placed in a container 51 of the reaction apparatus shown in FIG. 8A, and there is carried out hybridization reaction of the two DNA probes fixed on the polystyrene fine particles with the single-stranded DNA sample. During the reaction, the container 51 is held in a heat sink 53 and maintained, for example, at 45° C. by a temperature-controlling system composed of a temperature-measuring element 55, a controller 56 and a peltier element 54. Owing to the hybridization reaction, as shown in FIG. 7B, the two kinds of the fine particles 76 and 76' are combined by hybrids between each of the DNA probes 77 and 77' and the single-stranded DNA sample 78 to form aggregations of the fine particles in the solution.

Figure 8B:
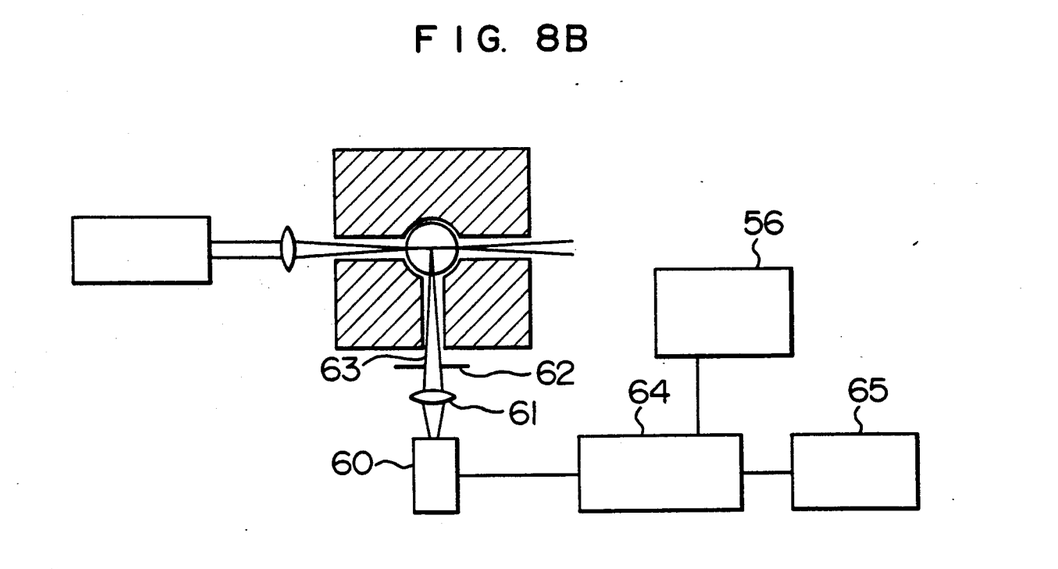

After completion of the hybridization reaction, S1 nuclease is added to the reaction mixture to carry out enzymatic treatment, whereby cleavage reaction of the mismatch portion of each hybrid is carried out. When the base sequence of the DNA sample is normal, the hybrid permitting the formation of the aggregations is composed of two strands completely complementary to each other, and is not cleaved by S1 nuclease. On the other hand, when a disorder such as insertion or deletion of a base sequence or single base substitution exists in the above first or second region of the DNA sample, the hybrid permitting the formation of the aggregations contains a mismatch of complementary base sequence at the position of the disorder. Such a hybrid is cleaved at the mismatch portion by enzymatic treatment with S1 nuclease, so that the aggregations in the solution disappear or decrease in size. Therefore, measurement of the size of the aggregations after the above enzymatic treatment permits judgment of the existence of a mismatch and hence disorders in the target genomic substance. A more accurate method for detecting a mismatch can be realized by making a comparison between the sizes of the aggregations before and after the enzymatic treatment. The reaction apparatus described above has a laser beam source 57 for irradiation of the reaction mixture 52 in the reaction container 51 and a lens for incidence 58. In addition, as shown in FIG. 8B, it has a detecting system for measuring scattered light 63 from the reaction mixture which is composed of an iris 62, a condenser lens 61 and a photodetector 60. The intensity of the scattered light after the enzymatic treatment or the difference of the intensities of the scattered light before and after the enzymatic treatment is input to a data processor 64. In general, the larger the particle size of the aggregations in the solution, the higher the intensity of the scattered light. Therefore, the existence of disorders in the target genomic substance can be investigated by display in a data display device 65 of the above intensity of scattered light or the difference of the intensities of the scattered light before and after the enzymatic treatment.

The size of the aggregations of fine particles in the solution or its change can be known not only by the above-mentioned measurement of the scattered light but also by various other methods. In the reaction apparatus shown in FIG. 9, laser beams from a laser beam source 57 are modulated by a chopper 80. A photoacoustic signal due to the fine particles or their aggregations in the reaction mixture 52 is detected in a photoacoustic element 81. From the change of the photoacoustic signal thus detected, there can be investigated the change of the aggregations caused by the enzymatic treatment, and hence the existence of disorders in the DNA sample. A condenser microphone can also be used as the photoacoustic element 81.

As to the particular size dependence of the intensity of the scattered light and the intensity of the photoacoustic signal in the case of light having a definite wavelength, there is a resonance range in which the intensity of the signal is increased at a specific particle size. Therefore, by choosing a size of the fine particles so that the size of the resulting aggregations is in said resonance range, there can be increased the difference between the signal intensity obtained when the fine particles are aggregated and the signal intensity obtained when the fine particles are dissociated, and hence the detection sensitivity can be improved.

Although the first and second DNA probes complementary to the adjacent first and second regions, respectively, on base sequence of the DNA sample were used in the disorder-detecting method explained with reference to FIGS. 7 to 9, three or more DNA probes may be used. It is also possible to use DNA probes complementary to a plurality of separate regions on the base sequence of the DNA sample. In the latter case, all strands between fine particles formed by hybridization reaction contain at least one single-stranded portion. Therefore, four kinds of nucleotide triphosphates which constitute DNA are added after carrying out hybridization reaction by addition of the DNA sample, and complementary chain elongation reaction is carried out by the use of the single-stranded portion as a template to bring the strands into double-stranded state. Then, enzymatic treatment with S1 nuclease is carried out as in the preceding examples, and the change of aggregations is detected. Also in the case of such a procedure, when there is a disorder of the base sequence in the plurality of the aforesaid separate regions of the DNA sample, a mismatch portion remains at a corresponding position of the strands brought into double-stranded state, and hence is cleaved by the enzymatic treatment, resulting in disappearance of the aggregations or a change of their size.

Figure 9:
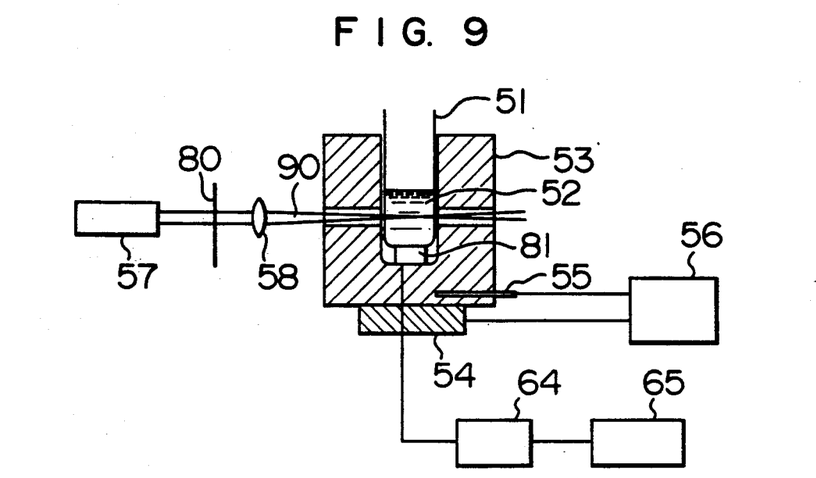
FIG. 9 is a longitudinal sectional view of an apparatus used in still yet another example of the present invention.

The reaction apparatuses shown in FIG. 8 and FIG. 9, respectively, have a temperature-controllable reaction container, a light irradiation system, and a detecting system. Therefore, they make it possible to carry out the whole process of reaction and detection continuously in the same place. Accordingly, there can be realized an automatic apparatus which does not require much labor in the whole procedure and is easy to operate. Furthermore, a high throughput required in diagnostic apparatuses can be realized by adding a vibrator to the reaction container to reduce the reaction time by vibration.

Although sequence disorders in DNA fragments were detected in all the examples described above, the same detection can be conducted also for RNA fragments. In this case, RNase A is suitable as a nuclease used for cleaving the mismatch portion of a hybrid.

What is claimed is:

1. A method for detecting disorders in genomic substances comprising the steps of:
preparing a solution containing first particles each having plural pieces of a first single-stranded nucleic acid probe attached thereto and a large number of second particles each having plural pieces of a second single-stranded nucleic acid probe attached thereto, said first and second single-stranded nucleic acid probes being complementary to a first region and a second region, respectively, on an objective genomic substance, which are exclusive of each other and contiguous to each other;
adding a single-stranded denatured product of the target nucleic acid to the solution;
forming aggregations of the first and second particles in the solution by hybridization of the denatured target nucleic acid added with particles with attached first and second single-stranded nucleic acid probes;

digesting the solution containing the aggregations with a nuclease which cleave the non-complementary-mismatch-containing portion of the double strand of each hybrid which had permitted the formation of the aggregations, in the vicinity of a mismatch-localized region;

measuring the size of the aggregations in the digested solution; and determining the degree of mismatching between the complementary base sequences of the target nucleic acid and the first or second single-stranded nucleic acid probe using the size information of the aggregations in the digested solution.

2. A method according to claim 1, wherein the difference of the sizes of the aggregations in the solutions before and after the digestion is measured.

3. A method according to claim 1, wherein the measurement of the size of the aggregations in the solution is conducted by measuring the intensity of scattered light generated by irradiation of the solution with laser beams.

4. A method according to claim 1, wherein the measurement of the size of the aggregations in the solution is conducted by detecting a photoacoustic signal given by irradiation of the solution with modulated laser beams.

* * * * *